(12) United States Patent
Saenz Villalobos et al.

(10) Patent No.: US 12,611,285 B2
(45) Date of Patent: Apr. 28, 2026

(54) WIRELESS DEVICES, SYSTEMS, AND METHODS FOR ENDOSCOPIC POSITIONING

(71) Applicant: BOSTON SCIENTIFIC SCIMED, INC., Maple Grove, MN (US)

(72) Inventors: Gonzalo Jose Saenz Villalobos, Alajuela (CR); Gian Franco Loo Fuchs, San Jose (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 581 days.

(21) Appl. No.: 18/108,247

(22) Filed: Feb. 10, 2023

(65) Prior Publication Data

US 2023/0255722 A1    Aug. 17, 2023

Related U.S. Application Data

(60) Provisional application No. 63/309,246, filed on Feb. 11, 2022.

(51) Int. Cl.
A61B 90/00        (2016.01)
A61B 17/00        (2006.01)
(Continued)

(52) U.S. Cl.
CPC .......... A61B 90/39 (2016.02); A61B 17/1114 (2013.01); A61B 2017/0034 (2013.01);
(Continued)

(58) Field of Classification Search
CPC .............. A61B 17/083; A61B 17/1114; A61B 17/1227; A61B 17/128; A61B 17/29;
(Continued)

(56) References Cited

U.S. PATENT DOCUMENTS 6,579,311 B1 *   6/2003   Makower ......... A61B 17/12109
                                                                        606/8
10,702,354 B2    7/2020   Wada et al.
                         (Continued)

FOREIGN PATENT DOCUMENTS

EP        1561420 A2      8/2005
WO        0144837 A2      6/2001
WO      2011100625 A2     8/2011

OTHER PUBLICATIONS

International Search Report and Written Opinion dated May 15, 2023 for International Application No. PCT/US2023/012796.
(Continued)

*Primary Examiner* — Jocelin C Tanner
(74) *Attorney, Agent, or Firm* — Seager , Tufte & Wickhem, LLP

(57)        ABSTRACT

A locator system deployable at a target site in a first anatomical structure and identifiable from within a second anatomical structure. The locator system includes a signal generator and a tissue-engagement member. The tissue-engagement member engages tissue at the target site so that a delivery system may deliver the locator system and be withdrawn without disturbing the position of the locator system with the tissue-engagement member engaging tissue at the target site. The signal generator may be powered by a wireless energy source, such as a battery, or radio waves. The locator system may be deployed at a target site within a patient's intestines, and identified from within the patient's stomach to create an anastomosis between the stomach and the target site.

20 Claims, 6 Drawing Sheets

(51) Int. Cl.
*A61B 17/11* (2006.01)
*A61F 2/04* (2013.01)

(52) U.S. Cl.
CPC ................. *A61B 2017/1103* (2013.01); *A61B 2017/1139* (2013.01); *A61B 2090/3912* (2016.02); *A61B 2090/3945* (2016.02); *A61F 2002/045* (2013.01)

(58) Field of Classification Search
CPC .......... A61B 2017/00221; A61B 2017/00278; A61B 2017/0034; A61B 2017/00349; A61B 2017/00818; A61B 2017/1103; A61B 2017/1139; A61B 2017/1125; A61B 90/39; A61B 90/30; A61B 2090/3908; A61B 2090/3912; A61B 2090/3945; A61B 2090/3991; A61B 2090/309; A61B 2090/304; A61B 2090/306; A61F 2002/045; A61F 5/0089
USPC ......................... 606/205, 155, 157, 153, 151
See application file for complete search history.

(56) References Cited

U.S. PATENT DOCUMENTS

| | | | |
|---|---|---|---|
| 10,912,566 | B2 | 2/2021 | Dayton et al. |
| 10,952,733 | B2 | 3/2021 | Baron et al. |
| 11,020,214 | B2 | 6/2021 | Gupta et al. |
| 11,529,143 | B2 | 12/2022 | Walsh et al. |
| 2003/0050534 | A1* | 3/2003 | Kazakevich ......... A61B 1/0607 600/179 |
| 2005/0182318 | A1* | 8/2005 | Kaji ...................... A61B 90/39 600/424 |
| 2011/0017217 | A1* | 1/2011 | Wood ................... A61M 16/04 128/207.14 |
| 2019/0298401 | A1 | 10/2019 | Gupta et al. |
| 2019/0298559 | A1* | 10/2019 | Gupta ................ A61B 17/1114 |
| 2020/0364575 | A1 | 11/2020 | Griffin |
| 2021/0196106 | A1 | 7/2021 | Dayton et al. |
| 2021/0259691 | A1 | 8/2021 | Smith et al. |
| 2022/0061847 | A1 | 3/2022 | Pic et al. |
| 2022/0061848 | A1 | 3/2022 | Saenz Villalobos et al. |
| 2022/0096198 | A1 | 3/2022 | Lynch et al. |
| 2022/0183670 | A1 | 6/2022 | Montenegro et al. |
| 2022/0192670 | A1 | 6/2022 | Fleury et al. |

OTHER PUBLICATIONS

Lee et al., "An Advanced RFID-Based System to Localize Gastric and Colon Cancers during Laparoscopic Surgery," Surgical Endoscopy, vol. 35, pp. 139-147, 2021.

* cited by examiner

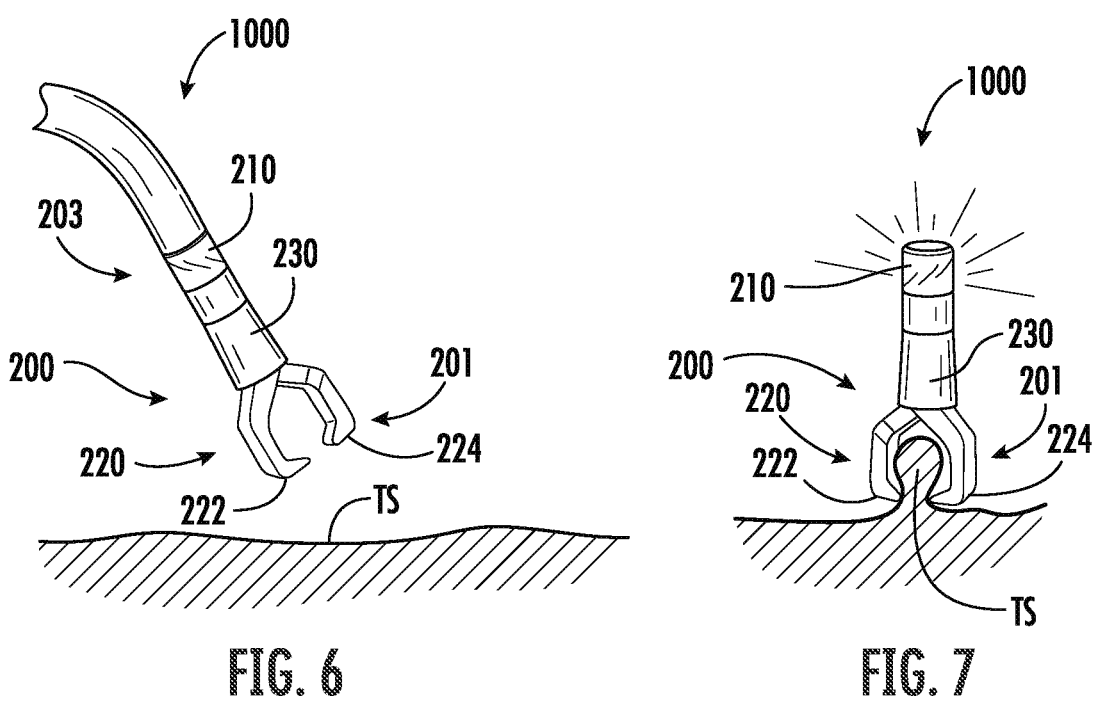
FIG. 6
FIG. 7
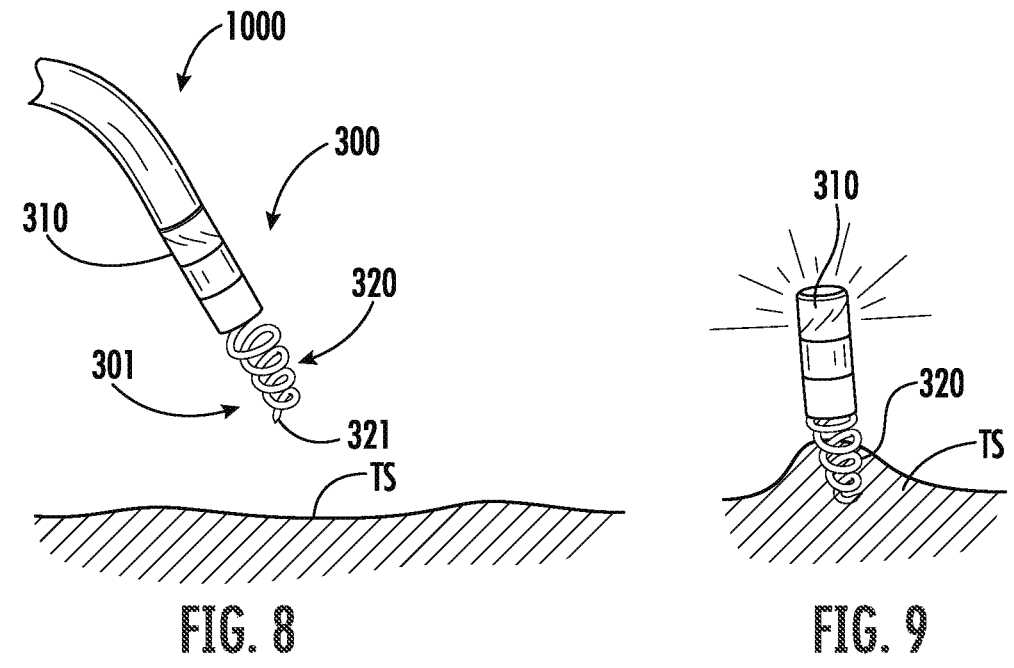
FIG. 8
FIG. 9

WIRELESS DEVICES, SYSTEMS, AND METHODS FOR ENDOSCOPIC POSITIONING

CROSS-REFERENCE TO RELATED APPLICATIONS

This application claims the benefit of priority of U.S. Provisional Application No. 63/309,246, filed Feb. 11, 2022, the entire disclosure of which is hereby incorporated by reference herein for all purposes.

FIELD

The present disclosure relates generally to the field of medical devices for use within a body. In particular, the present disclosure relates to medical devices, systems, and methods for use with endoscopic procedures. Even more particularly, the present disclosure relates to medical devices, systems, and methods for facilitating positioning of a device within the body, such as facilitating identification of the location of a target site within the body.

BACKGROUND

Viewing, locating, and manipulating anatomies, devices, and/or anatomies containing one or more devices from within a body may be difficult. During a procedure within the body, such as an endoscopic procedure within a body lumen (not involving cutting open the body), a medical professional may need to externally locate a particular anatomical structure of and/or position within the body. Locating a desired anatomical structure of and/or position within a body may be difficult due to a lack of or low amount of illumination, and/or intervening anatomy, and/or the shape and/or configuration of various portions of the body. For instance, procedures within body lumens such as the intestines present lengthy regions of the anatomy which may be difficult to differentiate from outside the body. Various locating devices may be provided within the body. However, manipulation of devices within the body with respect to such locating devices (e.g., to perform a procedure with the device being manipulated, and/or to withdraw a delivery device for the locating device) may cause such locating devices to be displaced, thereby interfering with the purpose and function of such locating devices.

It is with respect to these and other considerations that the present improvements may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a system for performing a procedure at a target site includes a locator system having a beacon and a tissue-engagement member; a delivery system configured to deliver and deploy the locator system to a target site at a first anatomical structure; and instruments for performing a procedure at the target site; where the locator system is separable from the delivery system upon delivery to the target site and engagement of the tissue-engagement member with tissue at the target site. In some embodiments, the procedure is the creation of an anastomosis. In some embodiments, the instruments include a cutting tool and a grasping tool deliverable to a second anatomical structure.

In some embodiments, the beacon is a light powered by a wireless energy source.

In some embodiments, the tissue-engagement member extends away from the beacon and is configured to engage tissue to hold the beacon with respect to the target site.

In some embodiments, the tissue-engagement member includes a pair of grasper arms or a tip embeddable within tissue.

In some embodiments, the system further includes visualization system deliverable to a second anatomical structure and capable of identifying the beacon through tissue between the first anatomical structure and the second anatomical structure.

In some embodiments, the system includes a delivery device including a flexible elongate tubular member within which the locator system is deliverable to a target site. In some embodiments, the instruments are deliverable within the delivery device to a second anatomical structure.

In some embodiments, the system includes a stent having a lumen therethrough and configured to extend through tissue of the first anatomical structure and a second anatomical structure. In some embodiments, the stent has a lumen therethrough for creating an anastomosis between the first anatomical structure and the second anatomical structure at the target site within the first anatomical structure.

In some embodiments, the system includes a tissue approximator configured to hold tissue of the first anatomical structure and a second anatomical structure in apposition at the target site. In some embodiments, the tissue approximator is extendable through tissue of the first anatomical structure and the second anatomical structure to hold the tissue of the first anatomical structure and the second anatomical structure in apposition at the target site. In some embodiments, the tissue approximator includes a first expanded anchoring end extending into the first anatomical structure, and a second expanded anchoring end extending into the second anatomical structure, where the first and second expanded ends of the tissue approximator are configured to hold tissue of the first anatomical structure and tissue of the second anatomical structure in apposition.

In some embodiments, the locator system is removable through tissue cut by the cutting tool.

In some aspects, a system for performing a procedure at a target site includes a locator system having a beacon and a tissue-engagement member, the tissue-engagement member engageable with tissue at a target site on a first anatomical structure; and an anastomosis system having at least one of a stent or a tissue approximator extending through tissue of the first anatomical structure at the target site and tissue of a second anatomical structure to hold the tissue of the first anatomical structure in apposition with tissue of the second anatomical structure; where the locator system is removable through an opening in or through the first anatomical structure or may slough off the target site to be expelled naturally through the body. In some embodiments, the stent has a lumen therethrough for creating an anastomosis between the first anatomical structure and a second anatomical structure.

In some embodiments, the anastomosis system includes both a stent, and a tissue approximator adjacent the stent.

In some embodiments, the system includes a tissue approximator having a first expanded anchoring end extending into the first anatomical structure, and a second expanded anchoring end extending into a second anatomical structure, where the first and second expanded ends of the tissue approximator are configured to hold tissue of the first anatomical structure and tissue of the second anatomical structure in apposition.

In some embodiments, the instruments of the anastomosis system include a cutting tool capable of cutting an opening through tissue of at least a second anatomical structure, and a grasping tool capable of extending through the opening in the second anatomical structure to grasp the first anatomical structure and draw the first anatomical structure into apposition with the second anatomical structure.

In some embodiments, the anastomosis system further includes a visualization system deliverable to a second anatomical structure and capable of identifying the beacon through tissue between the first anatomical structure and the second anatomical structure.

In accordance with various principles of the present disclosure, a method of creating an anastomosis between a first anatomical structure and a second anatomical structure includes delivering a locator system to a target site in the first anatomical structure using a delivery system; engaging a tissue-engagement member of the locator system with tissue at the target site, separating the delivery system from the locator system to deploy the locator system, and withdrawing the delivery system from the locator system to leave the locator system in place at the target site, where the locator system is anchored with respect to the target site by the tissue-engagement member so that withdrawal of the delivery system does not disturb the position of the locator system with respect to the target site.

In some embodiments, the method includes identifying a beacon of the locator system from within a second anatomical structure.

In some embodiments, the method includes creating an anastomosis between the first anatomical structure and the target site in the second anatomical structure. selected or calculated not predetermined.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows:

FIG. 6 illustrates a perspective view of an example of an embodiment of a locator system formed in accordance with various principles of the present disclosure, being delivered to a target site.

FIG. 7 illustrates a perspective view of an example of an embodiment of a locator system as in FIG. 6 in a deployed position.

FIG. 8 illustrates a perspective view of an example of an embodiment of a locator system formed in accordance with various principles of the present disclosure, being delivered to a target site.

FIG. 9 illustrates a perspective view of an example of an embodiment of a locator system, such as in FIG. 8, in a deployed position.

DETAILED DESCRIPTION

Figure 1:
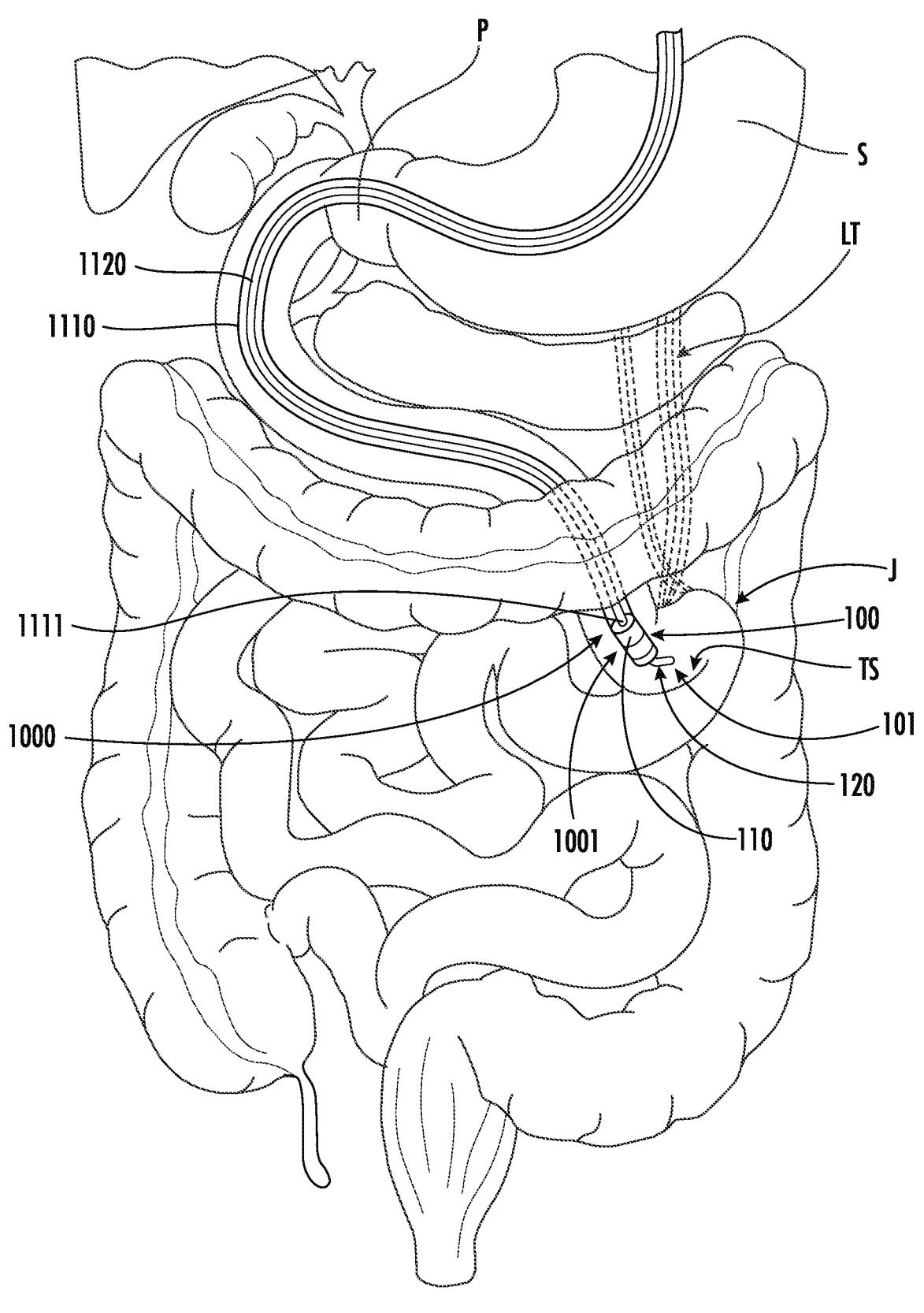
FIG. 1 illustrates a perspective view of an embodiment of an implantable locator system formed in accordance with various aspects of the present disclosure and positioned in a schematic representation of a gastrointestinal environment.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and "distal" refers to the direction or location furthest from the user, such as when using the device (e.g., introducing the device into a patient, or during implantation, positioning, or delivery), and/or closest to a delivery device. "Longitudinal" means extending along the longer or larger dimension of an element. "Central" means at least generally bisecting a center point and/or generally equidistant from a periphery or boundary, and a "central axis" means, with respect to an opening, a line that at least generally bisects a center point of the opening, extending longitudinally along the length of the opening when the opening comprises, for example, a tubular element, a strut, a channel, a cavity, or a bore.

A number of medical procedures require identification of the location of an anatomical structure, such as an organ or a tissue wall, and then delivering medical instruments to such location to perform a procedure on or at the identified location (e.g., "target site" or "target tissue" or "target tissue site", etc., the present disclosure being applicable to any such location, reference to any one such designation being applicable to the other designations without intent to limit unless otherwise indicated). It may desirable to be able to locate the identified location at a later time (e.g., after the delivery system for the locator system has been removed), and/or from another location within the body, such as to perform a procedure after identification of the anatomical location. Non-limiting examples of procedures which may be performed include various medical procedures which involve moving a tissue wall (e.g., a body lumen wall or the wall of an organ) to a desired position, such as relative to another tissue wall (e.g., a body lumen wall or the wall of an organ). For instance, various procedures may be performed by entering the gastrointestinal (GI) tract through a first organ or structure (such as the esophagus, stomach, duodenum, small intestine, large intestine, or peritoneal cavity), and delivering an anchor or stent to adjacent organs or lumen or tissue structures (such as an adjacent portion of the GI tract, the bile duct, the pancreatic duct, the gallbladder, the pancreas, cysts, pseudocysts, abscesses, and the like). Typically, it is necessary to penetrate both a first tissue wall (e.g., a wall of an organ or a first body lumen), through which access is established, and a second tissue wall (e.g., of a wall of an organ or a second body lumen) along or adjacent or at the target for the procedure. A stent or other tissue anchor may be deployed between adjacent body lumens, organs, or other structures, such as to maintain tissue walls in apposition, and/or to create an anastomosis, as indicated by the procedure. Tissue anchors may be used, in addition to the stent(s), to secure adjacent tissues or organs, such as before a stent is deployed, and may be left in place after the stent has been deployed.

Endoscopic procedures have been used to create a connection, such as an anastomosis, between the stomach and a certain part of the intestines through a gastroenteral anastomosis. For example, conditions of a disease may be benefitted by bypassing a portion of the duodenum, such as by creating an anastomosis, e.g., about 150 cm or greater from the pylorus, between the stomach and the small intestines (with a distal portion of the duodenum, or with the jejunum). In gastric outlet obstruction, a gastrojejunostomy serves the purpose of draining the contents of the stomach into the jejunum below/distal to the obstructed/dysfunctional duodenum. A gastrojejunostomy procedure may also serve as a minimally invasive and possibly reversible treatment option for patients with metabolic disease, by creating an anastomosis between the stomach and the jejunum to bypass the duodenum, with accompanying desired metabolic effects. In this manner, absorption of stomach contents (e.g., food and other nutrients) in the duodenal portion may be bypassed and nutrients from such contents may not be absorbed, or uptake or absorption may delayed, as such contents travel from the stomach through the small bowel, promoting patient weight loss and possible controlling or resolving type-2 diabetes.

Gastroenteral anastomoses, and other procedures within the body, may be created surgically, either endoscopically (gastroscopically or laparoscopically) or through an open surgical procedure. Endoscopic procedures, such as gastroenteral anastomoses, present various challenges, including the need to endoscopically locate a desired position (which may be referenced herein as a "target site" or "target tissue site"), such as in the intestines via the gastric lumen. Ultrasound and/or fluoroscopy procedures provide images through the anatomical walls (e.g., gastric and enteral walls). However, although ultrasound is useful for imaging tissue, ultrasound may not image inorganic materials used to identify tissue as readily. Although fluoroscopy is well suited for viewing dense materials, such as those from which medical instruments are made, contrast mediums used with fluoroscopy may dissipate as the target tissue is located and may thus need to be reintroduced.

Another solution involves several devices that work in the following manner First, a beacon system, which includes a light at the distal end of a flexible elongate member (such as a guidewire or tubular element), is inserted, such as with an endoscope, to the desired location for the procedure (e.g., where the connection of the intestines with the stomach is intended to be made). The endoscope is withdrawn, leaving the light in place. Then, the endoscope is re-inserted into the body (e.g., parallel to the flexible elongate member with the light at the distal end thereof) and one or more instruments for performing the procedure are inserted, such as to make an incision in the stomach wall and into the peritoneum. The light is visualized, or otherwise located, to identify the target site for the procedure and the procedure may thus be performed at the desired target site. For instance, once in the peritoneum, the physician locates the desired section of the small intestines with the aid of the light therein that can be seen from outside the intestinal wall. The outside of the small intestines is grasped and brought together with the stomach. A stent may then be deployed to connect the small intestines and the stomach, thereby creating the anastomosis.

The above-described solution using a light to locate a target site for a procedure also presents some challenges. For instance, during the initial steps of the procedure, after the guidewire is located at the desired location, the endoscope needs to be retracted from the body while maintaining the location of the light within the body at the desired location. Retraction of the endoscope must be coordinated with advancement of the flexible elongate member on which the light is positioned in order to maintain the original, desired position of the light. Such procedure may be difficult to perform accurately, and may be prone to affect the final position of the light, and thus the location at which the one or more instruments for performing the procedure are to be advanced (e.g., portion of the small intestines at which the anastomosis with the stomach is to be formed), which is an important factor for the success of the process.

The present disclosure relates to devices, systems, and methods useful in performing a procedure, e.g., an endoscopic, laparoscopic, and/or open surgical procedure, within the body by initially identifying the target site for the procedure with a locator system, deploying the locator system at the target site, and then locating the locator system to perform the procedure at the desired target site identified by the locator system. In some aspects, the devices, systems, and methods may be used to create an anastomosis such as a gastrojejunal anastomosis. For example, devices and systems described herein may aid gastrojejunal anastomosis placement by reliably and repeatably locating a desired position in a patient's gastrointestinal system, e.g., distinguishing a position in the jejunum, such as proximal or distal or adjacent to the Ligament of Treitz. Additionally, devices and systems herein may allow for a medical professional to locate, grasp, hold, and/or cut a portion of the stomach and small bowel during a gastrojejunal anastomosis procedure. Optionally a stent or other conduit may be placed across the bypass bridging the walls of the stomach and jejunum where the openings are created. The stent or conduit may assist with establishing or maintaining the anastomosis open until it is stable. The stent may or may not be subsequently removed.

It will be appreciated that various principles of the present disclosure may be applied to devices, systems, and methods for performing other procedures within a patient's body with the use of a locator system and locator system delivery and deployment system as disclosed herein. Thus, although the systems and devices and methods described herein are described with respect to a gastrointestinal system, it may be understood that devices and systems and methods in accordance with the present disclosure may be advantageous for use in any other procedures, such as, without limitation, those involving grasping, manipulation, or cutting of tissue (e.g., a body lumen and/or other sensitive tissue structures). Moreover, it should be understood that the systems and devices and methods described herein may be used with other regions of the anatomy, such as anywhere selective location of tissue is through other tissue walls and/or is blind.

In accordance with various principles of the present disclosure, a locator system is positioned at a target site and separated from the delivery system upon deployment, thereby removing the need for coordinating removal of the endoscope with maintaining the locator system in the desired location. In some aspects, the locator system is delivered with a delivery system that delivers and attaches the locator system to the target site and deploys the locator system in the desired location within the body. The delivery system, including any deployment devices, may then be removed leaving just the locator system in place engaged with tissue at the target site. Optionally, before or after a procedure (e.g. an anastomosis) has been performed with respect to the target site, the locator system is retrievable (e.g., through the newly created pathway of the anastomosis). The locator system includes a signal generator which is identifiable from within other portions of the body to locate the target site, and a tissue-engagement member to hold the locator system in place with respect to the target site. It will be appreciated that terms such hold, anchor, secure, maintain, etc., may be used interchangeably herein without intent to limit. In some embodiments, the tissue-engagement member extends away from the signal generator and is configured to engage tissue to hold the signal generator with respect to the target site. It will be appreciated that reference may be made herein to signal generator, locator, remote device, beacon, guide, signal, emitter, light, etc., interchangeably and without intent to limit. Moreover, it will be appreciated that reference to "at" is intended to include at and about the vicinity of (e.g., along, adjacent, etc.), unless otherwise indicated.

In accordance with various principles of the present disclosure, a locator system is configured to be separable from a delivery and deployment system with which the locator system is delivered and deployed. For instance, the locator system may be configured to be unattached to other components extending proximally thereto, such as components extending from proximal locations (including, without limitation, outside the body) to the target site. The locator system may be engaged with tissue at the target site with any of a variety of tissue-engagement members. For instance, a tissue-engagement member configured to grasp tissue at the target site where the locator system will be positioned can be performed through clipping or grasping, such as with a pair of arms or jaws or by an anchoring tip capable of embedding within tissue (a corkscrew type tip), or other form of tissue-engaging structure known or heretofore known to those of ordinary skill in the art. In some embodiments, the tissue-engaging structure extends from an end of the signal generator and is configured to engage with tissue (e.g., target tissue) to hold the signal generator in a position extending away from the tissue-engaging structure and the tissue, such as without interference of the signal generator. It will be appreciated that the tissue-engagement member may alternately be referenced herein as a tissue fastener or clip or other mechanical securing device (e.g., a hemostatic clip, clamp, grasper, basket, gripper, magnet, adhesive, etc.), without intent to limit. It will further be appreciated that terms such as couple, engage, grasp, hold, clasp, clip, anchor, attach, affix, secure, etc. (and other grammatical forms thereof) may be used interchangeably herein without intent to limit. It will further be appreciated that the tissue which is engaged by the tissue-engagement member at the target site may be at the location at which a procedure such as an anastomosis is to be performed, or distal or proximal to such procedure, depending on the procedure being performed and the technique being used and the medical professional's specifications.

The locator system includes a signal generator (which may be referenced herein as a "beacon" without intent to limit) capable of being detected through tissue, such as the intestinal wall and the gastric wall. In some embodiments, the beacon is a light, such as a light-emitting diode, aka "LED". In some embodiments, the signal of the locator system is wireless. For instance, the beacon may emit a signal detected by another device, such as positioned within a different position in the body, to assist in navigating such other device to the target tissue site. Generation and emission of a signal may require a power source capable of being placed within a patient's body (e.g., biocompatible, small, safe, etc.). In accordance with various principles of the present disclosure, the beacon is wireless and separable from the locator delivery device so that retrieval of the locator delivery device does not interfere with the desired positioning of the locator system. The beacon may be powered by a wireless energy source or by a compact energy source carried by or within the locator system.

Various embodiments of devices, systems, and methods for locating a position within a body will now be described with reference to examples illustrated in the accompanying drawings. Reference in this specification to "one embodiment," "an embodiment," "some embodiments", "other embodiments", etc. indicates that one or more particular features, structures, concepts, and/or characteristics in accordance with principles of the present disclosure may be included in connection with the embodiment. However, such references do not necessarily mean that all embodiments include the particular features, structures, concepts, and/or characteristics, or that an embodiment includes all features, structures, concepts, and/or characteristics. Some embodiments may include one or more such features, structures, concepts, and/or characteristics, in various combinations thereof. It should be understood that one or more of the features, structures, concepts, and/or characteristics described with reference to one embodiment can be combined with one or more of the features, structures, concepts, and/or characteristics of any of the other embodiments provided herein. That is, any of the features, structures, concepts, and/or characteristics described herein can be mixed and matched to create hybrid embodiments, and such hybrid embodiment are within the scope of the present disclosure. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. It should further be understood that various features, structures, concepts, and/or characteristics of disclosed embodiments are independent of and separate from one another, and may be used or present individually or in various combinations with one another to create alternative embodiments which are considered part of the present disclosure. Therefore, the present disclosure is not limited to only the embodiments specifically described herein, as it would be too cumbersome to describe all of the numerous possible combinations and subcombinations of features, structures, concepts, and/or characteristics, and the examples of embodiments disclosed herein are not intended as limiting the broader aspects of the present disclosure.

In the drawings, it will be appreciated that common features are identified by common reference elements and, for the sake of brevity and convenience, and without intent to limit, the descriptions of the common features are generally not repeated. For purposes of clarity, not all components having the same reference number are numbered. Moreover, a group of similar elements may be indicated by a number and letter, and reference may be made generally to one or such elements or such elements as a group by the number alone (without including the letters associated with each similar element). It will be appreciated that, in the following description, elements or components similar among the various illustrated embodiments with reference numbers under 1000 are generally designated with the same reference numbers increased by a multiple of 100 and redundant description is generally omitted for the sake of brevity. Moreover, certain features in one embodiment may be used across different embodiments and are not necessarily individually labeled when appearing in different embodiments.

Turning now to the drawings, an example of an embodiment of a locator system 100 and delivery system 1000 configured to deliver the locator system 100 to a target site TS are illustrated in FIG. 1 in a schematic representation of a gastrointestinal system. It will be appreciated that principles of the present disclosure may be applied to other anatomical sites and structures, reference being made to gastrointestinal locations and structures for the sake of convenience and without intent to limit. In the illustrated example of an environment, a locator delivery system 1000 may be inserted, such as through a natural orifice transluminal endoscopic surgery (NOTES) procedure (e.g., through the nose or mouth, and into the esophagus) into and through the stomach S, through the pylorus P, and into the duodenum D. The locator system 100, which is generally delivered at the distal end 1001 of the locator delivery system 1000, is advanced by the locator delivery system 1000 to the desired target site TS for the locator system 100. The locator delivery system 1000 and locator system 100 may be advanced with the use of a control handle at a proximal end of the locator delivery system 1000 (not shown, but which may be any suitable control handle known to those of ordinary skill in the art, the details of which do not limit and are not critical to the present disclosure). Peristaltic migration through the GI system may also assist with advancing the locator delivery system 1000 and locator system 100. In the example of an environment illustrated in FIG. 1, the target site TS is in the jejunum J, such as adjacent, proximal, or distal to the Ligament of Treitz LT. A section of the jejunum J may be selected as a "target site TS" at a distance from the pylorus P at which an anastomosis between the jejunum J and the stomach S is to be formed (such as determined by a medical professional). The locator delivery system 1000 may assist in identifying and selecting the target site TS, such as with the use of optical/visualization elements known to those of ordinary skill in the art (e.g., a camera, scope, fiber optics, fluoroscopy, etc., the details of which do not limit and are not critical to the present disclosure). The locator system 100 is advanced by the locator delivery system 1000 to the target site TS. Once the locator system 100 has reached the target site TS, the locator system 100 is deployed, and the locator delivery system 1000 may be withdrawn from the locator system 100. Instruments for creating an anastomosis between the target site TS and a section of the stomach S (preferably in proximity to the target site TS in the jejunum J) may then be inserted, such as through a NOTES procedure, into the stomach S, as described in further detail below.

In the example of an embodiment illustrated in FIG. 1, the locator delivery system 1000 includes a flexible elongate delivery member 1110 capable of being delivered to the target site TS through the body. The flexible elongate delivery member 1110 may be delivered through a lumen within a flexible elongate tubular member (e.g., a shaft, catheter, endoscope, etc.) known to those of ordinary skill in the art for transluminal delivery of devices through the body (in contrast with via open-surgery techniques). In some embodiments, the flexible elongate delivery member 1110 is delivered through an endoscope (not shown, but which may be any of a variety of endoscopes known to those of ordinary skill in the art, such as illustrated schematically in FIG. 3 and FIG. 4) with visualization and/or imaging abilities to facilitate location of the target site TS. The distal end 1111 of the flexible elongate delivery member 1110 is configured to engage the locator system 100 securely to deliver the locator system 100 to the target site TS without the locator system 100 disengaging from the flexible elongate delivery member 1110 during delivery to the target site TS. The flexible elongate delivery member 1110 may also be configured to release the locator system 100 to deploy the locator system 100 at the target site TS and to allow withdrawal of the locator delivery system 1000 therefrom. In some embodiments, a separate controller 1120 operatively engages the locator system 100 to control movement of the locator system 100 with respect to the target tissue at the target site TS (e.g., to engage and/or secure the locator system 100 with respect to the target site TS). In some embodiments, the controller 1120 is an additional flexible elongate member extending through a lumen through the flexible elongate delivery member 1110 to operatively engage the locator system 100. The controller 1120 may have a proximal end via which movement of the controller may be transferred to the locator system 100.

The controller 1120 may be releasably operatively engaged with an element of the locator system 100 so that the controller 1120 may be disengaged from the locator system 100 once the locator system 100 has been deployed.

In accordance with various principles of the present disclosure, a locator system 100 extends distally from the distal end 1001 of the locator delivery system 1001, and includes a beacon 110 and a tissue-engagement member 120. The beacon 110 may be any of a variety of devices emitting a signal locatable through anatomical tissue. In some embodiments, the beacon 110 includes one or more light-emitting-diodes (LED's). Tissue-engagement member 120 is configured to grasp tissue (as described in further detail below, with reference to FIG. 5, FIG. 6, FIG. 7, and FIG. 8 so that the beacon of the locator device remains in place at the target site TS while the beacon delivery system 1000 is withdrawn from the target site TS. In some embodiments, the tissue-engagement member 120 extends distally from the locator delivery system 1000 towards a distal end 101 of the locator system 100. The locator delivery system 1000 thus delivers the locator system 100 in a position ready to engage target tissue at the target site TS.

Figure 2:
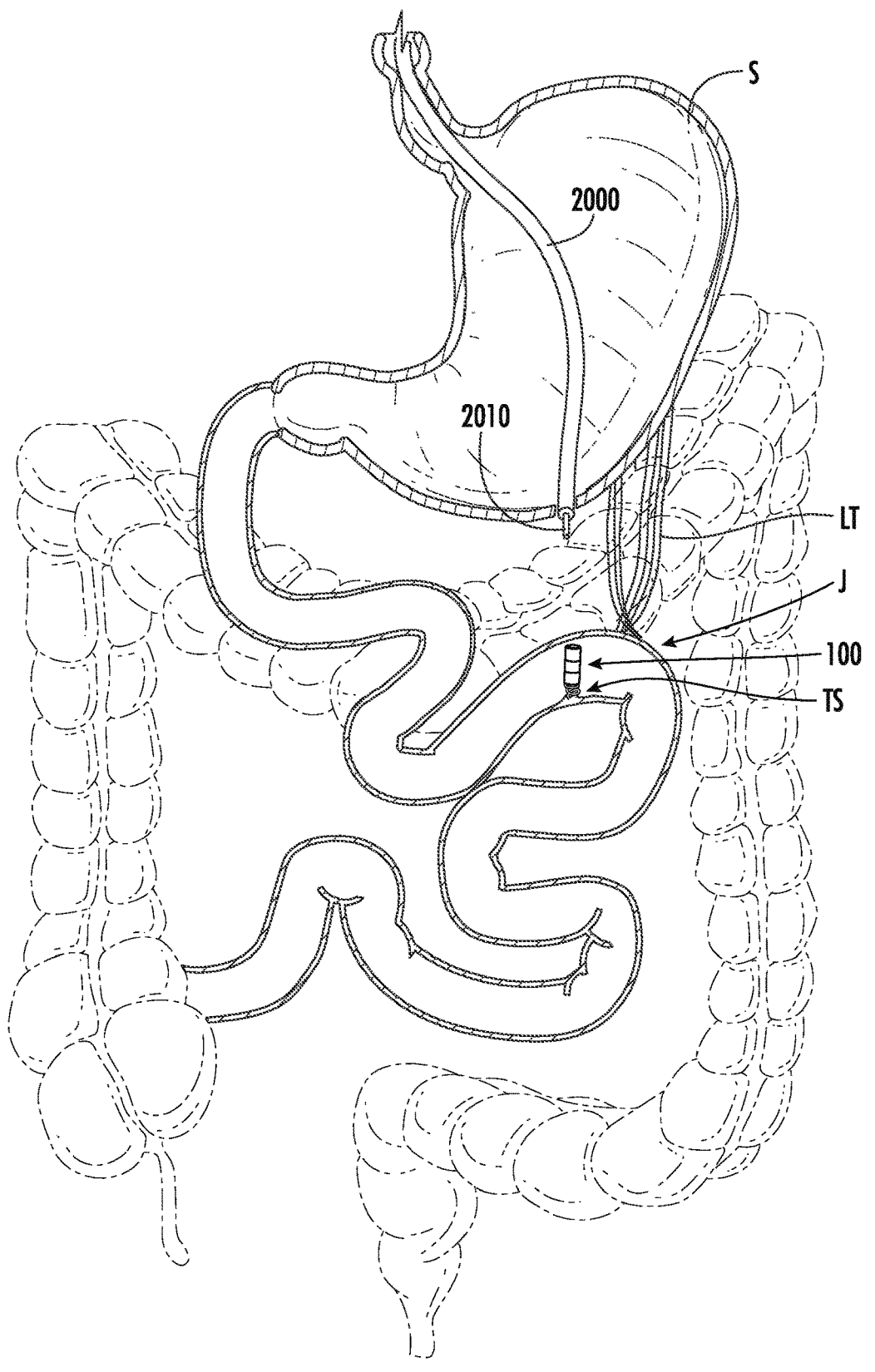
FIG. 2 illustrates a view similar to that of FIG. 1, but with the large intestine shown in phantom, and with an example of an embodiment of a locator system deployed at a target site, and a delivery system delivering instruments to reach the target site.

Once the locator system 100 has been delivered to the target site TS, the tissue-engagement member 120 thereof is actuated to be engaged with tissue at or along the target site TS. The locator system 100 may then be released from the locator delivery system 1000, and deployed at the target site TS. The locator delivery system 1000 may then be withdrawn from the target site TS (e.g., from a first anatomical structure). A procedural instrument delivery system 2000, such as illustrated in FIG. 2, may then be inserted into the GI system, such as through a NOTES procedure, and into the stomach S. It will be appreciated that the procedural instrument delivery system 2000 may include common delivery components as in the locator delivery system 1000. For instance, the endoscope may be used in the delivery system 2000 as in the locator delivery system 1000. The delivery system 2000 includes a visualization system by which the beacon 110 of the locator system 100 may be visualized to locate the target site TS. For instance, the delivery system 2000 may include an endoscope or the like (e.g., a colonoscope) with a camera or other visualization system as known or heretofore known by those of ordinary skill in the art, the details of which do not limit and are not critical to principles of the present disclosure. Once the target site TS has been located, various instruments, tools, devices, etc. (such terms being used interchangeably herein without intent to limit) may be delivered by the delivery system 2000 to create an anastomosis between the target site TS and an appropriate location along the stomach S.

Figure 3:
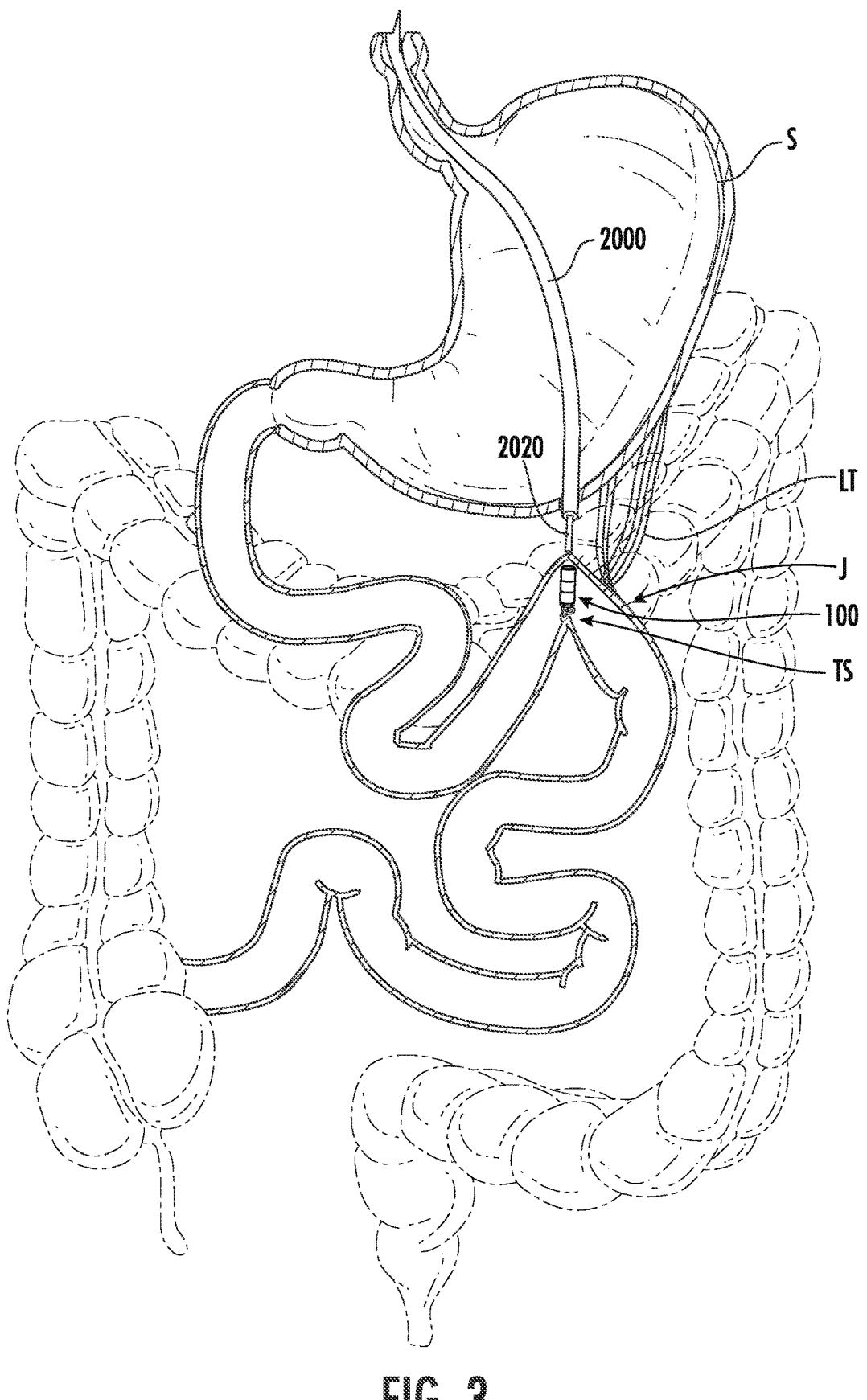
FIG. 3 illustrates a view similar to that of FIG. 2, with instruments illustrated being delivered in FIG. 2 reaching the target site.

For instance, a cutting tool 2010 may be delivered by the delivery system 2000 to create an opening through the wall of the stomach S in the region of the target site TS (as guided by the beacon 110), as illustrated in FIG. 2. It will be appreciated that the term "cutting" is to be understood herein in the broad sense of creating an opening, and a "cutting tool" is to be understood as any tool known to those of ordinary skill in the art capable of creating an opening in tissue, such as a blade, cauterization tool (e.g., with a cauterization blade), needle, scissors, ablation device, other energy delivery device, etc., the present disclosure not being limited specifically to cutting in any narrow sense of such term. A grasping tool 2020 (any grasper known to those of ordinary skill in the art capable of grasping tissue, such as an end effector, clips, snare, etc.) may be delivered by the delivery system 2000 (e.g., through a working channel through which the cutting tool 2010 has been delivered, and after withdrawal of the cutting tool 2010; or through a different working channel of the delivery system 2000; or as a part of the cutting tool 2010; or otherwise), and extended through the hole in the stomach S cut by the cutting tool 2010, as illustrated in FIG. 3. The grasping tool 2020 is extended towards the jejunum J to grasp the portion of the jejunum J with the target site TS therein (as identified by the locator system 100), and to draw such portion of the jejunum J to the stomach S. The jejunum J may be held in position with respect to the stomach S and an anastomosis may be formed therebetween in any desired manner known or heretofore known by those of ordinary skill in the art.

Figure 4:
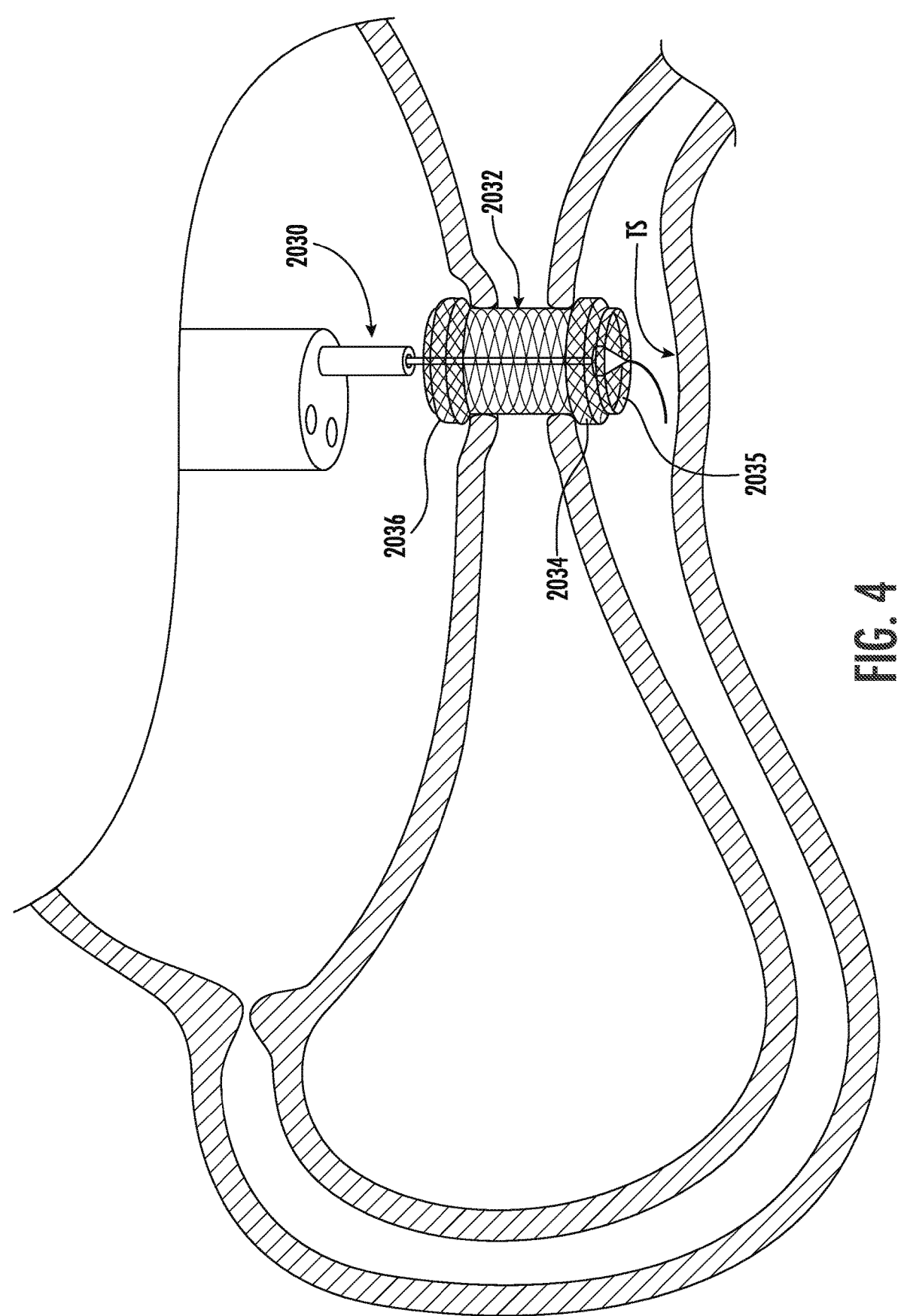
FIG. 4 illustrates an isolated view of the portions of the stomach and jejunum illustrated in FIG. 3 as being drawn together, with an anastomosis therebetween.
Figure 5:
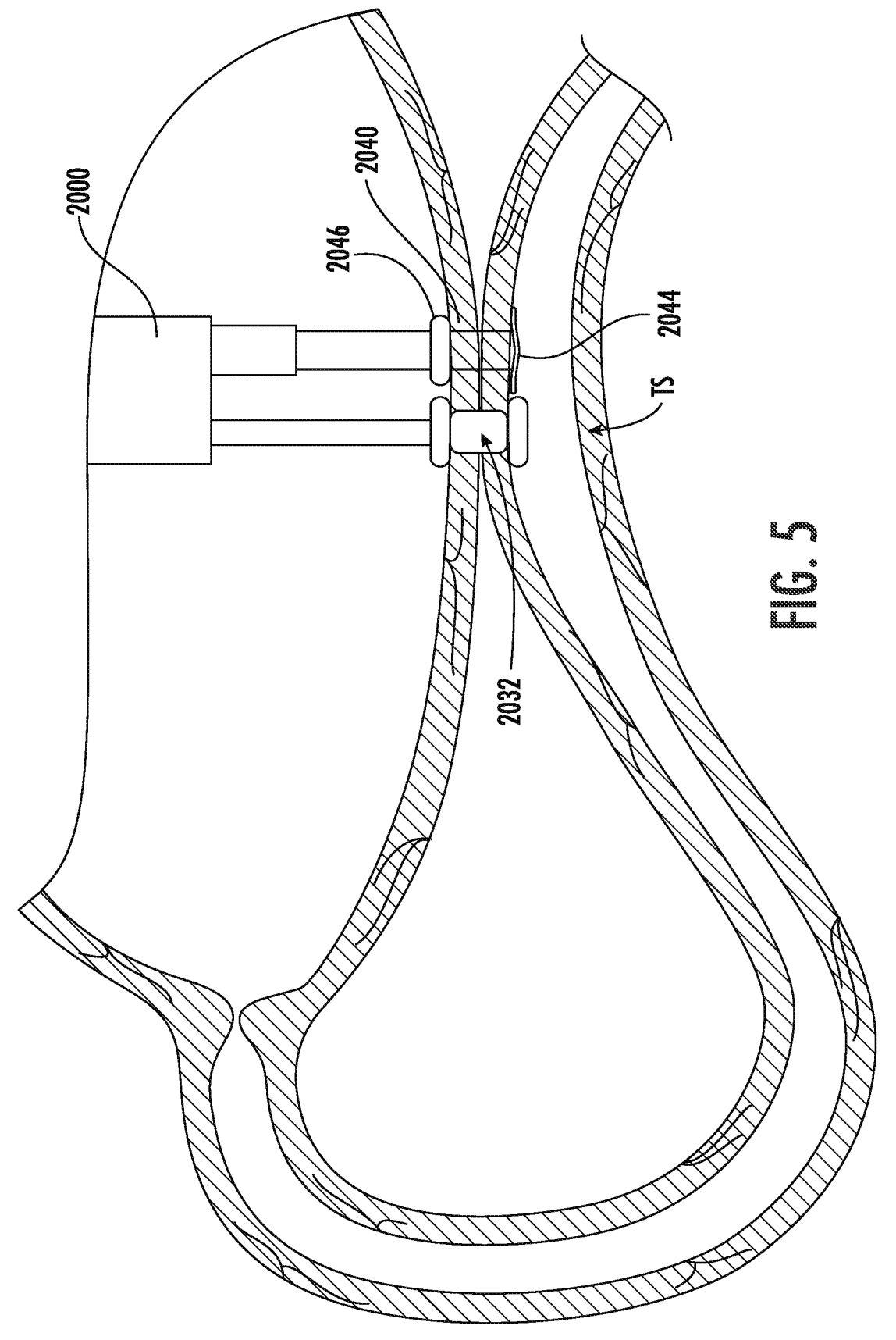
FIG. 5 illustrates a view similar to that of FIG. 4, but with a tissue approximator holding the stomach and jejunum tissue walls in apposition.

For instance, in some embodiments, an anastomosis system 2030 may be delivered to the apposed portions of the jejunum J and stomach S to form an anastomosis therebetween. In some embodiments, such as illustrated in FIG. 4, the anastomosis system 2030 may deliver a stent 2032 configured to hold the apposed portions of the jejunum J and stomach S together (e.g., with a retention member 2034 within the jejunum J, and a retention member 2036 within the stomach S) and to create an anastomosis therebetween (e.g., via a lumen 2035 through the stent 2032). In some embodiments, the stent 2032 may be deployed through the opening formed by the cutting tool 2010. In some embodiments, such as illustrated in FIG. 5, the jejunum J and stomach S may be held in close apposition by a tissue approximator 2040 for deployment of a stent 2032 through such tissue walls to form an anastomosis (such as described above with respect to the example of an embodiment illustrated in FIG. 4). In some embodiments, the tissue approximator 2040 extends through apposed tissue walls and is configured to hold tissue walls in apposition such as with an expanded tissue anchoring end 2044 within the jejunum J, and an expanded tissue anchoring end 2046 within the stomach S. The example of an embodiment of a tissue approximator 2040 as illustrated in FIG. 4 may be delivered by the delivery system 2000 and/or the anastomosis system 2030 (which may share features and/or structures). In some embodiments, the tissue approximator 2040 is deployed through the opening formed by the cutting tool 2010. In such instance, the anastomosis system 2030 may include a cutting tool 2010 to create an opening in apposed walls of the jejunum J and stomach S adjacent the tissue approximator 2040, as well as a deployment device to deploy the stent 2032 therethrough.

It will be appreciated that a locator system formed in accordance with various principles of the present disclosure need not be permanently implantable. In some embodiments, the locator system may be retrieved before or after the anastomosis is completed. For instance, the locator system may be retrieved through a natural opening (e.g., via which the locator system was delivered and deployed) or an opening created by the cutting tool 2010 in the area of the target site TS. In some embodiments, once the anastomosis between the jejunum J and the stomach S has been formed, the locator system 100 may be removed (e.g., as the last step), and thus optionally is not present, such as illustrated in FIG. 4 and FIG. 5. Therefore, biological compatibility may not be as rigorous as would be necessary for an implantable device.

Examples of embodiments of locator systems 200, 300 formed in accordance with various principles of the present disclosure and used as described above are shown in further detail in FIG. 6, FIG. 7, FIG. 8, and FIG. 9.

As illustrated in FIG. 6 and FIG. 7, an example of an embodiment of a locator system 200 has a beacon 210 in the form of an LED coupled with a tissue-engagement member 220 having a pair of grasper arms 222, 224 (which may alternately be referenced as jaws, without intent to limit) extending from the distal end 201 of the locator system 200 to engage tissue at the target site TS. In some embodiments, the tissue-engagement member 220 is repositionable after being partially deployed. For example, the tissue-engagement member 220 may be configured to allow for the tissue-engagement member 220 to be releasably engaged (e.g., closed, but not locked, into engagement) with tissue when in a first configuration, and locked against opening out of engagement with tissue when in a second closed configuration. In some embodiments, the grasper arms 222, 224 are selectively movable away from each other to engage tissue at the target site TS therebetween, and movable towards each other to grasp engaged target tissue. The grasper arms 222, 224 may be hinged together (e.g., as a single piece), or separately formed and movable with respect to each other, such as by being pivotable about a pivot point. In some embodiments, the grasper arms 222, 224 are biased apart, and brought together to grasp tissue therebetween by being retracted within a capsule 230. The grasper arms 222, 224 may have one or more additional grasping feature, such as a sawtooth or crenulated profile or teeth, at ends and/or along edges of the grasper arms 222, 224.

As described above with reference to the example of an embodiment of a locator system 100 illustrated in FIG. 1, the locator system 200 is configured to be released from the delivery system 1000 to be deployed engaging tissue at the target site TS. In some embodiments, the locator system 200 is coupled to a controller (such as known to those of ordinary skill in the art, the details of which do not limit and are not critical to the present disclosure) engaged with the tissue-engagement member 220 to control movement of the grasper arms 222, 224. In some embodiments, the tissue-engagement member 220 is releasable from such controller to thereby also release the locator system 200 from the delivery device 1000. For instance, the controller may movably extend through the delivery system 1000 (e.g., for axial translation or rotation therethrough to control opening and closing and other movements of the grasper arms 222, 224) and be engaged with the grasper arms 222, 224 via a frangible connection. Such connection may be overcome and/or a threshold pressure may be exerted to separate a jointed (e.g., ball and yoke) connection to separate the tissue-engagement member 220, and thus the locator system 200, from the controller, and thus the delivery system 1000. In such embodiment, the locator may extend through a proximal end 203 of the locator system 200 to engage the tissue-engagement member 220, such as by extending through the beacon 210. It will be appreciated that other manners of disengaging the example of an embodiment of a locator system 200 illustrated in FIG. 6 and FIG. 7 to deploy the locator system 200 are within the scope and spirit of the present disclosure.

It will be appreciated that the present disclosure is not to be limited to a particular form or configuration of a tissue-engagement member. For instance, in the example of an embodiment of a locator system 300 illustrated in FIG. 8 and FIG. 9, the tissue-engagement member 320 thereof may be in the form of tip configured to be embedded in tissue (e.g., to anchor independently of another tip or arm), such as a helical or corkscrew-shaped anchor. The tissue-engagement member 320 extends distally away from the beacon 310 and may have a tissue-penetrating end 321 at the distal end 301 of the locator system 300. The tissue-penetrating end 321 is engaged with the target site TS and penetrated into the target site TS such as by rotation thereof. In some embodiments, the delivery system 1000 is engaged with the tissue-engagement member 320 to impart rotation to the tissue-engagement member 320 to be secured in tissue at the target site TS.

In some embodiments, a controller extends through the delivery system 1000 (and optionally through the beacon 310 as well) to operatively engage the tissue-engagement member 320 to rotate the tissue-engagement member 320 to be secured in tissue at the target site TS. Once the tissue-engagement member 320 is secured in place at the target site TS, the delivery system 1000 (and controller, if provided) is disengaged from the tissue-engagement member 320 and the locator system 300 to deploy the locator system 300. For instance, axial retraction of the delivery system 1000 from the locator system 300 may release an interference fit therebetween. It will be appreciated that engagement elements, such as ribs, may be provided between the delivery system 1000 (and/or a controller delivered by the delivery system 1000) to impart rotation from the delivery system 1000 (and/or controller) to the tissue-engagement member 320, yet which allow axial removal from the locator system 300. It will be appreciated that other manners of disengaging the example of an embodiment of a locator system 200 illustrated in FIG. 8 and FIG. 9 to deploy the locator system 300 are within the scope and spirit of the present disclosure.

It will be appreciated that a signal generator formed in accordance with various principles of the present disclosure includes a wireless energy source. For instance, in some embodiments, a signal generator includes a small transponder intended to light an LED. In some embodiments, the transponder is energized by electromagnetic energy generated externally. For instance, the transponder may be based on the functioning principal used for RFID (radiofrequency identification) technology. The RFID system may include an RFID tag in the beacon of the locator system of the present disclosure, and an external RFID reader. The RFID tag may have a transponder chip with an antenna, and an external RFID reader with an antenna. The RFID reader can be used to emit instructions (e.g., via radio waves) that are received and executed by the tags. For instance, the RFID reader may generate electromagnetic energy that activates the RFID tag (which harvests the energy) without any internal source of energy within the tag. Current transponder technology has proven to be manufactured at a small enough size to allow for this kind of technology to work within a body. Other applications of RFID technology may be used, as may be appreciated by those of ordinary skill in the art:

In some embodiments, a remote (wireless) LED, with a tissue-engagement member, is powered by a portable compact energy source, such as a battery. The battery may be carried within or by the locator. The battery need not fit inside a flexible elongate delivery member (e.g., an endoscope) if the locator is front loaded through the distal end of the flexible elongate delivery member prior to starting the procedure, and advanced to the target site as needed. The battery may be encapsulated and thereby isolated from the body. The battery should provide sufficient power to light the LED for the typical duration of the procedure, but need not provide power beyond such duration if the locator is removed at the end of the procedure. Examples of acceptable batteries include lithium-ion batteries dimensioned to be delivered transluminally (e.g., endoscopically), such as less than about 20 mm long and/or less than about 3 mm in diameter. Given the low voltage requirement of an LED and the short period of use, other circuiting options include use of a capacitor as an energy source, which may be even smaller than a typical battery.

In view of the above, the present disclosure describes a locator system which is delivered to a target site and deployed in a manner which allows withdrawal of the delivery system without disturbing the locator system, i.e., without affecting the position at which the locator system has been deployed at the target site. A procedure may then be performed with respect to the target site with tools at another anatomical location in the body, with the aid of a visualization device capable of identifying the target site by locating the beacon of the locator system. The locator system may be removed before completion of the procedure (e.g., removed before, during, or after the procedure is performed with respect to the target site), or may be left in the body to naturally slough off and be expelled naturally from the body. For instance, the locator system may be engaged with a target site on a first anatomical structure and removed through an opening created or already formed in the first anatomical structure.

Although embodiments of the present disclosure may be described with specific reference to medical devices and systems (e.g., endoscopic devices, accessory tools, and/or guidewires) inserted near or through a jejunum, or the like, it should be appreciated that such medical devices and systems may be used in a variety of medical procedures for navigating one or more devices through ductal, luminal, vascular, or body lumen anatomies, including, for example, interventional radiology procedures, balloon angioplasty/angiography procedures, thrombolysis procedures, urological or gynecological procedures, and the like. The medical devices herein may include a variety of medical devices for navigating body lumens, including, for example, catheters, ureteroscopes, bronchoscopes, colonoscopes, arthroscopes, cystoscopes, hysteroscopes, and the like. The disclosed medical devices and systems may also be inserted via different access points and approaches, e.g., percutaneously, endoscopically, laparoscopically, or combinations thereof.

It will be appreciated that the foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, engaged, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A system for performing a procedure at a target site, said system comprising:

a locator system comprising a beacon and a tissue-engagement member;

a delivery system configured to deliver and deploy said locator system to a target site at a first anatomical structure; and instruments for performing a procedure at the target site deliverable separately from said locator system;

wherein:

said locator system is attachable to the target site and separable from said delivery system upon delivery to the target site and engagement of said tissue-engagement member with tissue at the target site to remain deployed, attached to the target site.

2. The system of claim 1, wherein said beacon is a light powered by a wireless energy source.

3. The system of claim 1, wherein said tissue-engagement member is operably associated with and extends distally away from said beacon and is configured to engage tissue to hold said beacon with respect to the target site.

4. The system of claims 3, wherein said tissue-engagement member comprises a pair of grasper arms or a tip embeddable within tissue.

5. The system of claim 1, further comprising a visualization system deliverable to a second anatomical structure and capable of identifying said beacon through tissue between the first anatomical structure and the second anatomical structure.

6. The system of claim 1, further comprising a delivery device including a flexible elongate tubular member within which said locator system is deliverable to a target site and said instruments are deliverable to a second anatomical structure.

7. The system of claim 1, further comprising a stent having a lumen therethrough and configured to extend through tissue of the first anatomical structure and tissue of a second anatomical structure.

8. The system of claim 7, further comprising a tissue approximator configured to hold tissue of the first anatomical structure and the second anatomical structure in apposition at the target site.

9. The system of claim 1, further comprising a tissue approximator configured to hold tissue of the first anatomical structure and tissue of a second anatomical structure in apposition at the target site.

10. The system of claim 9, wherein said tissue approximator is extendable through tissue of the first anatomical structure and the second anatomical structure to hold the tissue of the first anatomical structure and the second anatomical structure in apposition at the target site.

11. The system of claim 1, wherein said locator system is removable from the first anatomical structure.

12. A system for creating an anastomosis at a target site, said system comprising:

a locator system comprising a beacon and a tissue-engagement member, said tissue-engagement member configured to be engaged with tissue at a target site on a first anatomical structure; and an anastomosis system comprising at least one of a stent or a tissue approximator configured to extend tissue of the first anatomical structure at the target site and tissue of a second anatomical structure to hold the tissue of the first anatomical structure in apposition with tissue of the second anatomical structure;

wherein said beacon is configured to be removable through an opening between the first anatomical structure and the second anatomical structure and is also configured to alternatively be removable by sloughing off the target site to be expelled naturally through the body.

13. The system of claim 12, wherein said anastomosis system comprises both a stent, and a tissue approximator adjacent said stent.

14. The system of claim 12, wherein said tissue approximator comprises a first expanded anchoring end configured to extend into the first anatomical structure, and a second expanded anchoring end configured to extend into the second anatomical structure, wherein said first and second expanded ends of said tissue approximator are configured to hold tissue of the first anatomical structure and tissue of the second anatomical structure in apposition.

15. The system of claim 12, wherein said beacon is a light powered by a wireless energy source.

16. The system of claim 12, wherein said anastomosis system further comprises a cutting tool capable of cutting an opening through tissue of at least the second anatomical structure, and a grasping tool capable of extending through the opening in the second anatomical structure to grasp the first anatomical structure and draw the first anatomical structure into apposition with the second anatomical structure.

17. The system of claim 16, wherein said anastomosis system further comprises a visualization system deliverable to the second anatomical structure and capable of identifying said beacon through tissue between the first anatomical structure and the second anatomical structure.

18. A method of creating an anastomosis between a first anatomical structure and a second anatomical structure, said method comprising:

delivering a locator system including a beacon and a tissue-engagement member to a target site in the first anatomical structure using a delivery system;

engaging the tissue-engagement member of the locator system with tissue at the target site;

separating the delivery system from the locator system to deploy the locator system with the beacon engaged to tissue and separated from the delivery system; and withdrawing the delivery system from the locator system to leave the locator system in place at the target site;

wherein the locator system is anchored with respect to the target site by the tissue-engagement member so that withdrawal of the delivery system does not disturb the position of the locator system with respect to the target site.

19. The method of claim 18, further comprising identifying the beacon of the locator system from within a second anatomical structure.

20. The method of claim 19, further comprising creating an anastomosis between the first anatomical structure and the target site in the second anatomical structure.

\* \* \* \* \*